United States Patent [19]
Lurie et al.

[11] Patent Number: 5,588,422
[45] Date of Patent: Dec. 31, 1996

[54] METHODS AND PHARMACEUTICAL COMPOSITIONS FOR ENHANCED CARDIOPULMONARY RESUSCITATION

[75] Inventors: Keith G. Lurie; Barbara S. Gold, both of Minneapolis, Minn.

[73] Assignee: Regents of the University of Minnesota, Minneapolis, Minn.

[21] Appl. No.: 977,498

[22] Filed: Nov. 17, 1992

[51] Int. Cl.$^6$ ............................................. A61M 15/00
[52] U.S. Cl. ........................ 128/200.24; 128/202.28
[58] Field of Search .................. 128/200.24, 204.18, 128/205.13, 202.28, 202.29, 203.11, 28, 30, 30.2

[56] References Cited

U.S. PATENT DOCUMENTS

| | | | |
|---|---|---|---|
| 4,397,306 | 8/1983 | Weisfeldt et al. | 601/41 |
| 4,424,806 | 1/1984 | Newman et al. | 601/41 |
| 4,945,899 | 8/1990 | Sugiyama et al. | 128/28 |
| 4,955,375 | 9/1990 | Martinez | 128/207.15 |

FOREIGN PATENT DOCUMENTS 1651900  5/1991  U.S.S.R. .

OTHER PUBLICATIONS

Guidelines for CPR and Emergancy Cardiac Care (1992) J. Am. Med. Assoc. 268:2205–2211.
Neimann (1992) N. Eng. J. Med. 327:1075–1080.
Lurie et al. (1990) J. Am. Med. Assoc. 264:1661.
Cohen et al. (1992) J. Am. Med. Assoc. 267;2916–2923.
Flatau et al. (1982) Isr. J. Med. Sci. 18:878–882.
Kuhn (1978) Am. Heart J. 95;529–534.
Sibbald et al. 63:455–482.
Standards and Guidelines for Cardiopulmonary Resuscitation (CPR) and Emergency Cardiac Care (ECC) (1980) J. Am. Med. Assoc. 244:453–509.
Ambu® CardioPump™ Directions for use, pp. 1–8 Ambu, Intl A/S.
Kyobu Geka Jul. 1992 45(7);619–22 Journal Article (Abstract from Computer Search).

*Primary Examiner*—Aaron J. Lewis
*Attorney, Agent, or Firm*—Schwegman, Lundberg, Woessner & Kluth, P.A.

[57] ABSTRACT

Methods and pharmaceutical compositions for resuscitating patients suffering from cardiac arrest are disclosed. The methods comprise the performance of cardiopulmonary resuscitation techniques which result in active inducement of venous blood transport into the heart and arterial blood transport from the heart. During the performance of such techniques, the patient is administered with an amount of an arterial constrictor sufficient to increase arterial blood pressure and with an amount of a venodilator sufficient to enhance arterial blood flow to the brain and heart. Pharmaceutical compositions comprise both the arterial constrictor and venodilator present in a single formulation. The methods are found to both enhance patient survival and reduce heart and brain damage.

6 Claims, 1 Drawing Sheet

METHODS AND PHARMACEUTICAL COMPOSITIONS FOR ENHANCED CARDIOPULMONARY RESUSCITATION

BACKGROUND OF THE INVENTION

1. Field of the Invention

The present invention relates generally to methods and pharmaceutical compositions for the enhanced performance of cardiopulmonary resuscitation techniques. More particularly, the present invention relates to the administration of certain pharmaceutical compositions to a patient undergoing cardiopulmonary resuscitation techniques which result in the active transport of venous blood back to the patient's thorax and heart.

Sudden cardiac arrest is a major cause of death worldwide and can arise from a variety of circumstances, including heart disease, electrical shock and other trauma, suffocation, and the like. To enhance patient survival and reduce the likelihood of damage to the brain and heart resulting from oxygen deprivation, it is essential that a patient's respiration and blood circulation be restored as soon as possible. Over the years a number of artificial resuscitation techniques have been developed with such objectives in mind.

Of particular interest to the present invention, cardiopulmonary resuscitation (CPR) techniques have been developed which rely on external chest compression. In particular, manual CPR techniques rely on the manual application of a downward force on the patient's chest in order to force blood from the heart and expel air from the lungs. Ventilation by either mouth-to-mouth or mechanical techniques is performed concurrently with the chest compression in order to force air back into the patient's lungs. Such manual CPR techniques, however, partially rely on the natural elasticity of the chest in order to actively draw venous blood back into the heart, which turns out to be highly inefficient. Long term survival in cardiac arrest patients who have undergone standard CPR is usually below 10%.

In an effort to increase the survival chances of a cardiac arrest patient, advanced cardiac life support (ACLS) techniques have been developed. Such techniques often include the intravenous or endotracheal administration of fluids and drugs, such as epinephrine, during performance of CPR. Epinephrine is an arterial constrictor, and its use is intended to enhance patient blood pressure during the resuscitation process. Even with epinephrine, however, survival after cardiac arrest is poor. Such poor survival may result from a decrease in the delivery of oxygenated blood to portions of the heart caused by epinephrine.

Venodilators, such as nitroglycerin, are drugs which dilate the coronary arteries and improve blood flow to the heart. Such venodilators are often administered to patients at risk of heart attacks in order to increase blood flow to the heart and decrease the chance of the patient suffering an attack. The use of venodilators, however, is contraindicated during the performance of most cardiopulmonary resuscitation techniques, such as CPR, since such drugs can cause a significant decrease in patient blood pressure. As such, venodilators act predominantly on the veins, it is believed that the administration of such drugs to patients undergoing CPR would result in increased pooling of blood in the veins. Thus, although venodilators are frequently administered in combination with arterial constrictors patients suffering from heart disease, the administration of such a combination to patients undergoing CPR is not practiced. Nitroglycerin is used in clinical practice when the heart is contracting but not during ventricular fibrillation, when there is a chaotic heart rhythm and no effective cardiac contractibility or blood pressure. Nitroglycerin is not currently used when the heart is not beating at all, as in asystole or electromechanical dissociation (EMD).

An improved method of CPR, referred to as active compression/decompression (ACD) CPR, results in improved blood circulation through the heart and ventilation of the patient's lungs when compared to standard CPR methods. Such ACD CPR methods utilize a vacuum cup device which is applied to the anterior chest wall and which is used for alternately compressing and "actively" expanding the patient's chest to induce both ventilation and blood circulation. By "active" expansion, it is meant that the vacuum cup adheres to the patient's chest and provides an upward force on the chest wall to expand the thorax and heart. While initial results with ACD CPR show significant improvements in patient survival rates among at least certain patient populations, it would be desirable if such survival rates could be improved even further.

It would therefore be desirable to provide improved methods and pharmaceutical compositions for performing CPR, where such methods and compositions would result in enhanced long term survival among at least certain populations of cardiac arrest patients. Such methods and compositions would preferably enhance blood circulation and delivery of oxygenated blood to patient tissue, particularly heart and/or brain tissue, without significant lessening of patient blood pressure. The compositions would preferably comprise commonly used drugs, particularly commonly used cardiovascular drugs, in novel formulations and under novel treatment regimens, preferably in combination with known CPR techniques.

2. Description of the Background Art

Conventional CPR and ACLS techniques are described in Guidelines for CPR and Emergency Cardiac Care (1992) J. Am. Med. Assoc. 268:2205–2211, where the administration of epinephrine and other arterial constrictors during cardiac arrest and the performance of CPR is described. The administration of nitroglycerin is described for the treatment of acute angina pectoris and congestive heart failure, but not during cardiac arrest concurrently with CPR and ACLS. Niemenn (1992) N. Eng. J. Med. 327:1075–1080 describes the use of arterial constrictors during CPR as part of conventional and experimental ACLS techniques. ACD CPR techniques were first described in Lurie et al. (1990) J. Am. Med. Assoc. 264:1661 and have more recently been described in Cohen et al. (1992) J. Am. Med. Assoc. 267:2916–2923. Epinephrine is commonly administered to patients undergoing ACD CPR techniques. The treatment of a patient in cardiogenic shock with the administration of nitroglycerin in combination with high-frequency positive pressure ventilation is described in Flatau et al. (1982) Isr. J. Med. Sci. 18:878–882. Kuhn (1978) Am. Heart J. 95:529–534 describe the use of nitroglycerin and other vasodilators in treatment of congestive heart failure, but warn that such vasodilators may depress already critically low arterial blood pressure. U.S.S.R. patent 1651900 describes the direct injection of nitroglycerin into the heart muscle during artificial respiration and open-heart heart massage. Other references discussing CPR and artificial respiration include Sibbald et al. (1982) Surg. Clin. N. Am. 63:455–482; and Standards and Guidelines for Cardiopulmonary Resuscitation (CPR) and Emergency Cardiac Care (1980) J. Am. Med. Assoc. 244:453–509. The full disclosures of each of these references are incorporated herein by reference.

SUMMARY OF THE INVENTION

According to the present invention, methods and compositions are provided for resuscitating patients suffering from cardiac arrest, particularly patients experiencing ventricular fibrillation, asystole, electromechanical dissociation (EMD), and the like. The methods rely on active inducement of venous blood transport into the heart and arterial blood flow from the heart while ventilating the patient's lungs using closed chest techniques. Such simultaneous blood transport and ventilation can be achieved using known techniques, such as conventional CPR, or preferably using enhanced CPR techniques such as active compression and active expansion of the patient's chest (ACD CPR), alternate compression of the patient's chest and abdomen or lower extremities (IAC), and the like.

Concurrently with the inducement of blood flow and lung ventilation, the patient is administered with an amount of an arterial constrictor sufficient to increase the patient's arterial blood pressure and with an amount of a venodilator sufficient to enhance arterial blood flow to the patient's brain and heart. Preferably, the arterial constrictor and venodilator will be administered to the patient simultaneously as part of a novel pharmaceutical composition which forms a further aspect of the present invention.

Surprisingly, it has been found that the active transport of venous blood back into the heart significantly enhances patient blood pressure and prevents venous blood pooling which might otherwise be exacerbated by use of the venodilator. In this way, the patient can gain the benefits of enhanced cardiac and decreased cerebral blood flow which results from the administration of the venodilator. Lowering of the venous blood pressure by the venodilator will generally result in a larger pressure gradient between the arterial blood and the venous blood, resulting in improved tissue blood perfusion. Additionally, the venodilator can at least partially overcome the negative effects of the arterial constrictor which would otherwise reduce blood flow to the heart.

DESCRIPTION OF THE SPECIFIC EMBODIMENTS

Figure 1:
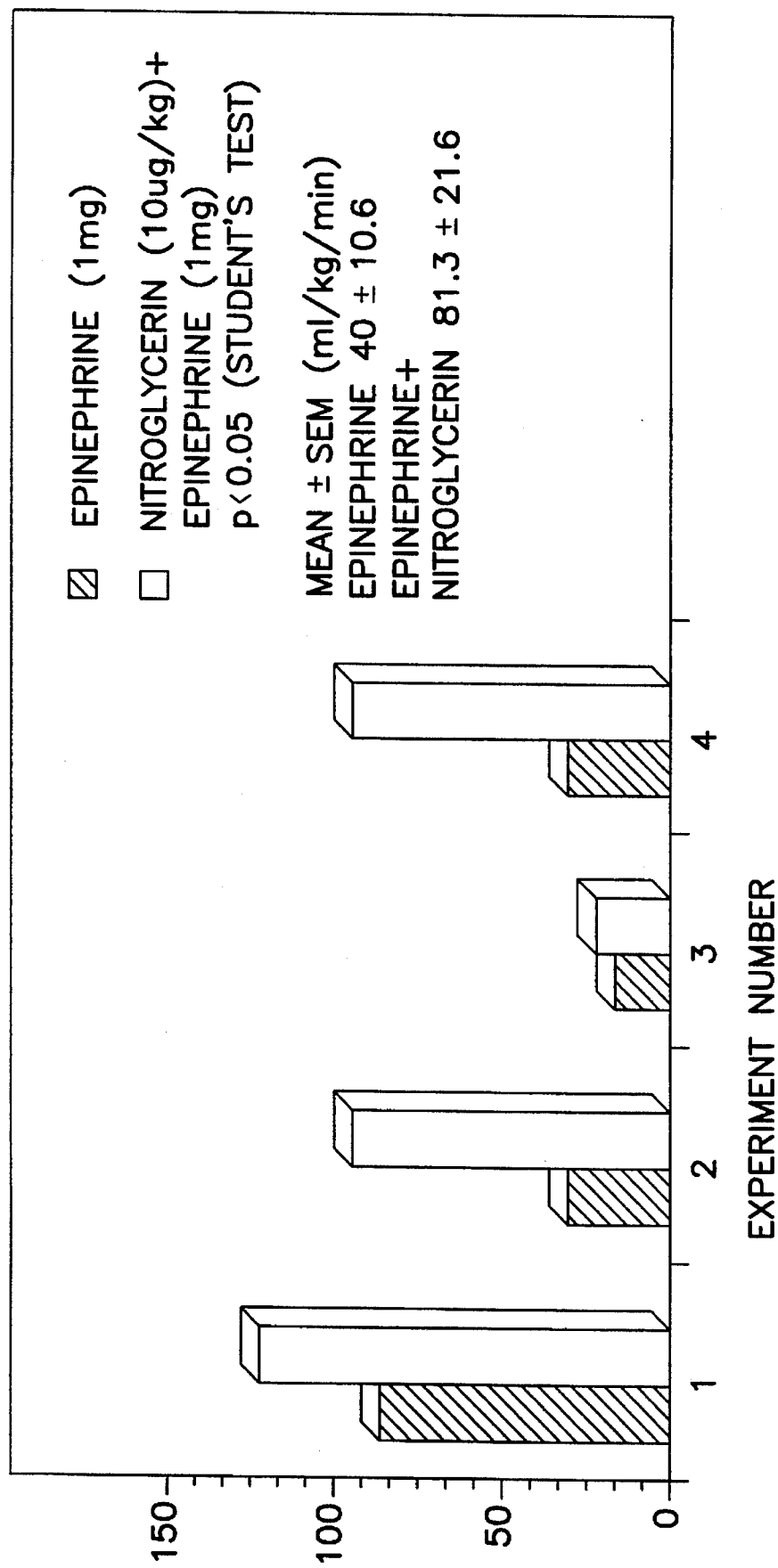
FIG. 1 is a graph of data which demonstrate the benefits associated with the administration of epinephrine and nitroglycerin compared to epinephrine alone during ACD CPR in test animals.

The present invention provides methods and pharmaceutical compositions useful for treating patients suffering from cardiac arrest. Cardiac arrest generally refers to conditions resulting in the loss of effective heart function and the loss of effective blood circulation. Specific conditions treatable by the present invention include ventricular fibrillation, characterized by rapid contractions and twitching of the heart muscle; asystole, characterized by the substantial absence of contractions of the heart; and electromechanical dissociation (EMD), characterized by the persistence of electrical activity in the heart without associated mechanical contractions.

The methods of the present invention comprise active inducement of blood transport and lung ventilation concurrently with the administration of certain drugs selected to both increase arterial blood pressure and to enhance arterial blood circulation. The active inducement of blood transport includes both the transport of venous blood from the extremities and abdomen, into the thorax and heart, as well as the transport of blood from the heart into the lungs and arterial system. Both the induced blood transport and the lung ventilation are preferably achieved by certain advanced CPR methods, such as ACD CPR, as described in Cohen et al. (1992), supra, and interposed abdominal compression (IAC), as described in Nymen (1992), supra. Induced blood transport and lung ventilation can be achieved, but to a lesser extent, with standard chest massage and CPR techniques. Optionally, additional measures will be taken to provide lung ventilation, such as use of an endotracheal tube, mouth-to-mouth resuscitation, or the like.

Particularly preferred is the use of ACD CPR techniques which combine external cardiac compression with active expansion of the patient's chest after each compression in order to lower the intrathoracic pressure and improve refilling of the heart. Such ACD CPR techniques may be conveniently performed using the CardioPump™ resuscitation device, commercially available from Ambu International A/S, Copenhagen, Denmark. The CardioPump™ device generally comprises a vacuum cup which is pressed against the patient's chest at a location generally over the patient's sternum. Using outstretched arms, the performer initiates chest compressions and decompressions at a rate generally in the range from about 80 to 100 per minute. The chest should be compressed at distance of about 38 to 51 mm for adults and 10 mm to 50 mm for children and infants, with the performer then pulling up on the vacuum pump to actively expand and decompress the chest, drawing venous blood into the heart and ventilating the lungs. Optionally, it may be desirable to periodically ventilate the patient using an endotracheal tube or mouth-to-mouth ventilation techniques in order to further enhance lung ventilation. Specific directions for use of the CardioPump™ device are provided in the publication entitled "Directions for Use Ambu® CardioPump™," published by Ambu International A/S Copenhagen, Denmark, the full disclosure of which is incorporated herein by reference.

The alternative IAC method for the inducement of blood transport and lung ventilation comprises alternately compressing the patient's abdomen and chest. One performer compresses the abdomen while a second performer (or machine) alternately compresses the chest, each at a rate of from 30 to 100 compressions per minute. A third person, or automated ventilator, will ventilate the patient's lung at from 12 to 20 ventilations per minute.

Another alternative procedure for active inducement of blood transport and lung ventilation is a variation of conventional mast trouser ventilation. Mast trouser ventilation is performed by placing the patient's lower extremities in inflatable "trousers" which are then inflated to force blood flow back into the thorax and heart. The method of the present invention alternates such "trouser inflations" with lung ventilation and chest compression to obtain the desired blood circulation and oxygenation.

A third alternate procedure for active inducement of blood transport is "vest" cardiovascular resuscitation where the patient is placed in a vest or chamber capable of pressurizing the chest to expel blood from the thorax. Such "vest" resuscitation techniques can be performed together with IAC CPR, as described above.

While these enhanced methods for CPR can by themselves improve the chances for patient survival when compared to conventional CPR, the present invention is based on the discovery that the chances for survival (with conventional CPR and in particular with the enhanced CPR techniques described above) can be further improved by administering to the patient both an arterial constrictor (inotrope) substance and a venodilator substance concurrently with the performance of the enhanced CPR procedure. Suitable arterial constrictors (inotropes) include epinephrine, dopamine, norepinephrine, vasopressin, α-adrenergic agonists, such as phenylephrine or methoxamine, and the like. Preferred is the administration of epinephrine at a total dosage (i.e., total amount given to the patient at one time point during the procedure; administration may be repeated at successive time points as described below) of from 0.5 mg to 20 mg, preferably from 1 mg to 10 mg. Suitable venodilators include nitroglycerin, and the like. Preferred is the administration of nitroglycerin at a total dosage of from 10 µg to 500 µg, preferably from 25 µg to 100 µg. The above dosages are the preferred ranges for adults and would be reduced somewhat for administration to children and infants.

The arterial constrictor substance and venodilator substance should be administered to the patient concurrently with or as soon as possible after the initiation of the enhanced CPR procedure, preferably being administered within from 0 to 60 minutes after such initiation, more preferably being administered from 0 to 10 minutes after such initiation. Both the initiation of CPR and the administration of the combination of constrictor and venodilator will begin within as shortly as possible after the cardiac arrest, with drug administration preferably beginning within 10 minutes of arrest. Administration of the combination of the constrictor and venodilator will preferably be repeated during procedures which last for more than 10 minutes, usually being repeated every 3 to 10 minutes.

The arterial constrictor and venodilator can be administered by any technique which assures rapid absorption into patient circulation, preferably being administered intravenously, endotracheally, or by other oral routes. Intravenous injections will usually be made to a peripheral vein in a conventional manner. Endotracheal administration may also be performed and is particularly suitable if an endotracheal tube has been placed in order to enhance lung ventilation and intravenous access is not immediately available. Devices and methods suitable for endotracheal administration of drugs according to the present invention are described in U.S. Pat. No. 4,693,243, the full disclosure of which is incorporated herein by reference. In the case of endotracheal administration, the total dosages described above for both the arterial constrictor and the venodilator will generally be increased in order to offset the inefficiencies of such an administration route. The dosages will usually be increased from two-fold to three-fold.

The arterial constrictor substance and the venodilator substance will preferably be administered together in a single dosage or bolus, but could less preferably be administered separately and/or sequentially to the patient. It would also be possible to administer the total desired dosage of each of the arterial constrictor and the venodilator in two or more discrete boluses, although such multiple administrations will generally be less preferred.

Pharmaceutical compositions according to the present invention thus comprise both the arterial constrictor substance and the venodilator substance present together in the above amounts in a pharmaceutically acceptable carrier, such as distilled water, saline, buffers, and the like. Pharmaceutical compositions will typically include a pharmaceutically acceptable preservative, and may include other components commonly employed in solutions suitable for intravenous and/or endotracheal administration. Methods for preparing such pharmaceutical compositions are well known in the art and described in more detail in various sources including, for example, Remington's Pharmaceutical Science, 15th Edition, Mack Publishing, Easton, Pa. (1980), which is incorporated herein by reference.

In addition to the arterial constrictor substance and the venodilator substance, the pharmaceutical compositions of the present invention may also include other active substances which are intended to enhance the therapeutic effectiveness of the composition. For example, the pharmaceutical compositions may also include mannitol present in an amount effective to reduce swelling of the brain, heart, and/or kidneys, based on mannitol's osmotic properties. Additionally, mannitol might also enhance patient blood pressure. Mannitol would be combined at a total dosage in the range from about 1 g to 100 g, preferably from 1 g to 50 g.

The pharmaceutical compositions of the present invention may optionally also include a calcium channel blocker, such as diltiazem, verapamil, nifedipine, and the like, present in an amount effective to inhibit calcium overload. Typically, diltiazem would be present at from 0.5 mg to 60 mg, preferably from 0.5 mg to 20 mg. Verapamil would be present at from 0.5 mg to 60 mg, preferably from 0.5 mg to 5 mg. Nifedipine would be present at from 0.2 mg to 10 mg, preferably from 0.5 mg to 5 mg.

The pharmaceutical compositions of the present invention may further comprise a $\beta_1$-adrenergic antagonist, such as metoprolol, present in an amount effective to inhibit the negative effect of epinephrine on oxygen consumption by the heart. Typically, metoprolol will be present in the composition at a total dosage in the range from 0.5 mg to 25 mg, usually from 0.5 mg to 5 mg.

The following examples are offered by way of illustration, not by way of limitation.

EXPERIMENTAL

Methods

Preparation. This study was approved by the University of Minnesota Committee on Animal Research and was performed in accordance with the Guiding Principles of the American Physiologic Society for the Use and Care of Laboratory Animals. Five beagles weighing 10–14 kg were anaesthetized with sodium pentobarbital (30 mg/kv i.v.). Supplemental sodium pentobarbital was administered as needed during surgery. Dogs were intubated with a 6F endotracheal tube and ventilated with 10 liters supplemental oxygen at a minute ventilation required to maintain arterial pH between 7.3 and 7.4. Arterial blood gas monitoring was performed every 30 minutes to ensure adequacy of ventilatory parameters. The chest was shaved and animals were placed in a supine position until immediately prior to induction of ventricular fibrillation. 5000U heparin was given intravenously prior to initiation of the study. After surgical exposure of the femoral arteries and veins, a 5 Fr pigtail catheter (Cordis Corp., Miami, Fla.) was placed into the right atrium and a 5 Fr bipolar catheter (Daig Corp., Minnetonka, Minn.) advanced under fluoroscopic guidance into the right ventricle. One pigtail catheter was also positioned in the apex of the left ventricle and a second in the descending thoracic aorta immediately distal to the left subclavian artery. Two 5 Fr sampling catheters (Cordis Corp., Miami, Fla.) were placed in the proximal iliac arteries, which served as the sites for collection of blood during microsphere injection. Esophageal pressure was measured using an Arndorfer multi-lumen water perfusion catheter (Medical Specialties, Inc., Greendale, Wis.) as an index of intrathoracic pressure. The catheter was continuously flushed with 5% dextrose at 15 cc/hr. Hemodynamic measurements using fluid-filled catheters were recorded on a multichannel Astro-Med recorder (Astro-Med, Inc., West Warwick, R.I.). Pressures from the thoracic aorta, right atrium and esophagus were recorded using Spectramed transducers (Spectramed, Inc., Oxnard, Calif.) referenced to the level of the right atrium. For analysis of hemodynamics during CPR with each technique, data were acquired at the end of each minute of each intervention. Maximum and minimum aortic and right atrial pressures obtained at end-expiration during compression (systole) and decompression (diastole) were averaged for six compressions over two respiratory cycles. Mean aortic and right atrial pressures were obtained electronically. 5000U heparin was given intravenously prior to initiation of the study. CPR Techniques.

ACD CPR was performed using a hand-held modified household plunger (i.d. 8 cm). At the base of the suction cup, a fluid-filled manometry system was constructed to allow monitoring of the force delivered to the chest wall during compressions. For each experiment, a new suction device was used to ensure adequate suction. Compression and active withdrawal of the plunger was continued with adequate suction to actively decompress the chest wall to an anteroposterior diameter approximately 10 percent beyond normal resting position ACD CPR was performed with the dogs in the left lateral oblique (45°) position. Compressions were delivered at the mid-ventricular level, determined fluoroscopically, slightly lateral to the sternum where adequate suction could be achieved.

Using a metronome, ACD CPR was performed at a rate of 80/minute with a 50% duty cycle. To ensure that the force of compressions was equal during all trials, two monitoring systems with continuous feedback to the person applying compressions were used. Direct measurements of force applied to the chest wall were made with the manometer constructed at the base of the plunger. In addition, esophageal manometry was used as an indirect assessment of intrathoracic pressure to record the degree of compression and decompression. The delivered force and resultant esophageal pressures were recorded on the Coulbourn recorder and also displayed for viewing by the operator throughout the experiment on an electronic oscilloscope. Using these techniques, 175–200 N force was applied to the chest wall with each compression resulting in approximately 45 mmHg intrathoracic pressure (end-expiratory), and 3 to 5 cm downward displacement of the chest wall.

Experimental Protocol. This protocol was designed to allow the comparison of tissue flows and hemodynamics with the administration of epinephrine (1 mg) alone, vasopressin (0.8 units/kg) alone, epinephrine (1 mg) and nitroglycerin (10 µg/kg) in combination, and vasopressin (0.8 units/kg) and nitroglycerin (10 µg/kg) in combination. In each of the five dogs, four ACD CPR interventions were performed, each lasting 8 minutes. Epinephrine was administered alone for 2 interventions and epinephrine and nitroglycerin in combination were administered for 2 interventions for each dog (n=4 dogs). Similarly, vasopressin was administered alone for 2 interventions and administered in combination with nitroglycerin for 2 interventions in 1 dog. The drugs, alone or in combination, were administered in alternating order and the order was determined randomly. Using this experimental design, hemodynamic and organ blood flow measurements during CPR were made multiple times in the same animal. Thus, comparison of tissue flows achieved with the various drug combinations could be made with each animal serving as its own control.

Before cardiac arrest, baseline hemodynamic measurements were obtained and radiolabeled microspheres were injected to determined control blood flows by methods previously described (17,18). During baseline measurements, saline was infused at 25 ml/hr and adjusted as needed to maintain mean right atrial pressure at 3–8 mmHg. Ventilatory support was continued throughout all experiments using hand-bag ventilation with 10 liters oxygen supplementation. Respirations were delivered at a rate of 16/min (1 breath every 5 chest compressions) at a constant tidal volume required to maintain the same minute ventilation delivered during surgical preparation. Ventricular fibrillation was induced by a single 5 second application of alternating current applied to a 5F bipolar electrode lead in direct contact with the endocardium of the right ventricle. After one minute of "down time," during which no CPR was performed, ACD CPR was initiated. The order in which the various drugs were administered to each dog was made randomly at the beginning of each experiment. Each drug and drug combination was administered as a bolus directly into the left ventricle at the onset of CPR. CPR with the first intervention was continued for 8 minutes during which blood flows and hemodynamics were measured. Radiolabeled microspheres were injected into the left ventricle three minutes after starting ACD CPR for each intervention. After 7.5 minutes of the first intervention, a 5 cc aliquot of blood was obtained from the left ventricle for blood gas analysis and to assess residual counts in the ventricle at the end of the intervention. After 8 minutes, CPR was stopped. After 1 minute of no CPR, the alternate CPR technique was performed for 8 minutes.

Tissue Flow Measurements. Regional blood flow was measured using 15 µm diameter microspheres with techniques similar to those previously reported and validated during CPR in dogs by Koehler et al. (1983) Circulation 67:266–275. The vials of microspheres were shaken and then dispersed by ultrasonic agitation. For each intervention, approximately $2 \times 10^6$ spheres were injected as a bolus into the left ventricle three minutes after the onset of chest compressions. Each injection was followed by a 10 cc flush of saline. Reference arterial blood samples were obtained in 30 second aliquots from both iliac arteries at a continuous rate of 5 cc/min/site using Harvard mechanical peristaltic pump (Harvard Apparatus, South Natick, Mass.). In order to maintain adequate volume status during the experiment, 1 unit of packed red blood cells was infused peripherally at the same rate as withdrawal from the iliac arteries. Animals were euthanized at the end of each experiment using bolus injections of potassium chloride. Organs were fixed in 10% formalin for sectioning and microsphere analysis.

Myocardium from the left ventricle was taken at the mid-ventricular level and sectioned into epicardial, and mid-myocardial regions. A total of 12 samples were available for each region. Brain tissue was sectioned into frontal, parietal and occipital regions, with each region yielding 4 samples. From each kidney, the outer 1–2 mm of tissue was taken for counting, yielding 12 renal cortical samples per experiment. Vials of blood and tissue were counted on a multichannel autogamma scintillation spectrometer. The energy windows used for $^{141}Ce$, $^{51}Cr$, $^{85}Sc$, $^{95}Nb$, and $^{46}Sr$ were 128–168, 304–348, 484–548, 718–804, and 834–1160 keV, respectively. Overlap of counts was subtracted to obtain corrected count values for each isotope using the method of differential spectroscopy (20). Tissue blood flow was then calculated by dividing tissue corrected counts by the total corrected counts/ml/min in the reference blood samples.

Statistical analysis. All values are expressed as mean values±standard error of the mean. Statistical analysis of regional blood flows and clearance of microspheres from the peripheral circulation was performed using the nonparametric Wilcoxon signed rank test because the standard deviation in the values was similar to the magnitude of the mean, suggesting the data were not normally distributed. For analysis of hemodynamic and arterial blood gas data, the paired Student's t test was used.

Results

The results are illustrated in FIG. 1. The results demonstrate that every time nitroglycerin was added to the arterial constrictor (epinephrine), blood flow to the heart was increased from 20–100% compared to the control in the absence of nitroglycerin. There was also a 30% improvement in brain flow when nitroglycerin was added to epinephrine. In an experiment with vasopressin and nitroglycerin, myocardial flow was 347±19.3 (mean±SEM) ml/kg/min in comparison to 254±15.5 ($p<0.01$) for vasopressin alone. Brain flow was also improved when nitroglycerin was administered together with epinephrine.

Although the foregoing invention has been described in some detail by way of illustration and example, for purposes of clarity of understanding, it will be obvious that certain changes and modifications may be practiced within the scope of the appended claims.

What is claimed is:

1. A method for resuscitating a patient suffering from cardiac arrest, said method comprising:
    (a) actively inducing venous blood transport into the heart and arterial blood transport from the heart;
    (b) ventilating the patient's lungs;
    (c) administering to the patient concurrently with said inducing and ventilating steps, a bolus of medicament comprising epinephrine and nitroglycerin in amounts of from 1 mg to 10 mg and 25 µg to 200 µg, respectively.

2. A method as in claim 1, comprising administering the bolus intravenously.

3. A method as in claim 1, comprising administering the bolus endotracheally.

4. A method as in claim 1, comprising including in said bolus 5 g to 50 g of mannitol.

5. A method as in claim 1, comprising including in said bolus a calcium channel blocker in an amount effective to inhibit calcium overload.

6. A method as in claim 1, comprising including in said bolus a beta-adrenergic antagonist in an amount effective to inhibit a negative effect of epinephrine on oxygen consumption by a patient's heart.

* * * * *